United States Patent
Chitre et al.

(10) Patent No.: US 7,894,915 B1
(45) Date of Patent: Feb. 22, 2011

(54) IMPLANTABLE MEDICAL DEVICE

(75) Inventors: Yougandh Chitre, Valencia, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 488 days.

(21) Appl. No.: 11/553,842

(22) Filed: Oct. 27, 2006

(51) Int. Cl.
*A61N 1/05* (2006.01)

(52) U.S. Cl. .................................................... 607/123

(58) Field of Classification Search ............... 607/36, 607/5, 9, 116, 119, 122, 123
See application file for complete search history.

(56) References Cited

U.S. PATENT DOCUMENTS

| | | | |
|---|---|---|---|
| 4,073,287 A * | 2/1978 | Bradley et al. .............. 600/373 |
| 4,256,115 A | 3/1981 | Bilitch |
| 4,693,253 A * | 9/1987 | Adams ........................... 607/4 |
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,119,832 A * | 6/1992 | Xavier ........................ 607/117 |
| 5,174,288 A * | 12/1992 | Bardy et al. .................... 607/2 |
| 5,249,574 A | 10/1993 | Bush et al. |
| 5,411,535 A * | 5/1995 | Fujii et al. ..................... 607/32 |
| 5,476,483 A | 12/1995 | Bornzin et al. |
| 5,529,067 A * | 6/1996 | Larsen et al. ............... 600/374 |
| 5,645,586 A | 7/1997 | Meltzer |
| 5,814,089 A | 9/1998 | Stokes et al. |
| 5,861,024 A * | 1/1999 | Rashidi ...................... 607/122 |
| 5,910,124 A | 6/1999 | Rubin |
| 6,096,064 A | 8/2000 | Routh |
| 6,141,588 A | 10/2000 | Cox et al. |
| 6,208,881 B1 * | 3/2001 | Champeau .................. 600/374 |
| 6,397,109 B1 * | 5/2002 | Cammilli et al. ............ 607/123 |
| 6,643,546 B2 * | 11/2003 | Mathis et al. .................. 607/9 |
| 6,647,292 B1 * | 11/2003 | Bardy et al. .................... 607/5 |
| 6,907,285 B2 * | 6/2005 | Denker et al. .................. 607/5 |
| 7,274,962 B2 * | 9/2007 | Bardy et al. .................... 607/5 |
| 7,389,134 B1 * | 6/2008 | Karicherla et al. .......... 600/375 |
| 7,422,585 B1 | 9/2008 | Eggers et al. |
| 7,496,409 B2 * | 2/2009 | Greenhut et al. ............ 607/116 |
| 2002/0082647 A1 | 6/2002 | Alferness et al. |
| 2002/0103510 A1 * | 8/2002 | Bardy et al. .................... 607/5 |
| 2002/0107549 A1 * | 8/2002 | Bardy et al. .................... 607/5 |
| 2002/0107559 A1 * | 8/2002 | Sanders et al. ............. 607/129 |
| 2003/0158584 A1 * | 8/2003 | Cates et al. .................... 607/2 |

(Continued)

FOREIGN PATENT DOCUMENTS

EP    1547648 A1    6/2005

(Continued)

OTHER PUBLICATIONS

NonFinal Office Action, mailed Mar. 17, 2009; Related U.S. Appl. No. 11/553,816.

(Continued)

*Primary Examiner*—Niketa I Patel
*Assistant Examiner*—Hiba El-Kaissi

(57) ABSTRACT

Techniques related to implantable medical devices (IMDs) are described. One such IMD includes first and second electrodes and a continuous body joined with and extending between the electrodes. Processing electronics are located within the body and are coupled with the first and second electrodes.

10 Claims, 7 Drawing Sheets

U.S. PATENT DOCUMENTS

| | | |
|---|---|---|
| 2003/0199955 A1 | 10/2003 | Struble et al. |
| 2003/0204206 A1 | 10/2003 | Padua et al. |
| 2004/0147973 A1 | 7/2004 | Hauser |
| 2004/0176673 A1 | 9/2004 | Wahlstrand et al. |
| 2004/0210292 A1* | 10/2004 | Bardy et al. ............... 607/119 |
| 2004/0249417 A1 | 12/2004 | Ransbury et al. |
| 2004/0249431 A1 | 12/2004 | Ransbury et al. |
| 2005/0043765 A1 | 2/2005 | Williams et al. |
| 2005/0149138 A1 | 7/2005 | Min et al. |
| 2005/0192639 A1* | 9/2005 | Bardy et al. ................... 607/5 |
| 2005/0228471 A1 | 10/2005 | Williams et al. |
| 2009/0149902 A1 | 6/2009 | Kumar et al. |

FOREIGN PATENT DOCUMENTS

| | | |
|---|---|---|
| WO | WO98/26840 | 6/1998 |
| WO | WO02/49669 A2 | 6/2002 |
| WO | WO02/49669 A3 | 6/2002 |
| WO | WO02/49714 A2 | 6/2002 |
| WO | WO2005/000398 A2 | 1/2005 |
| WO | WO2005/000398 A3 | 1/2005 |
| WO | WO 2007/103262 A2 | 9/2007 |

OTHER PUBLICATIONS

Final Office Action, mailed Oct. 29, 2009: Related U.S. Appl. No. 11/553,816.

NonFinal Office Action, mailed Sep. 29, 2009: Related U.S. Appl. No. 11/553,859.

NonFinal Office Action, mailed Jan. 22, 2010—Related U.S. Appl. No. 11/553,816.

Final Office Action, mailed Mar. 24, 2010—Related U.S. Appl. No. 11/553,816.

* cited by examiner

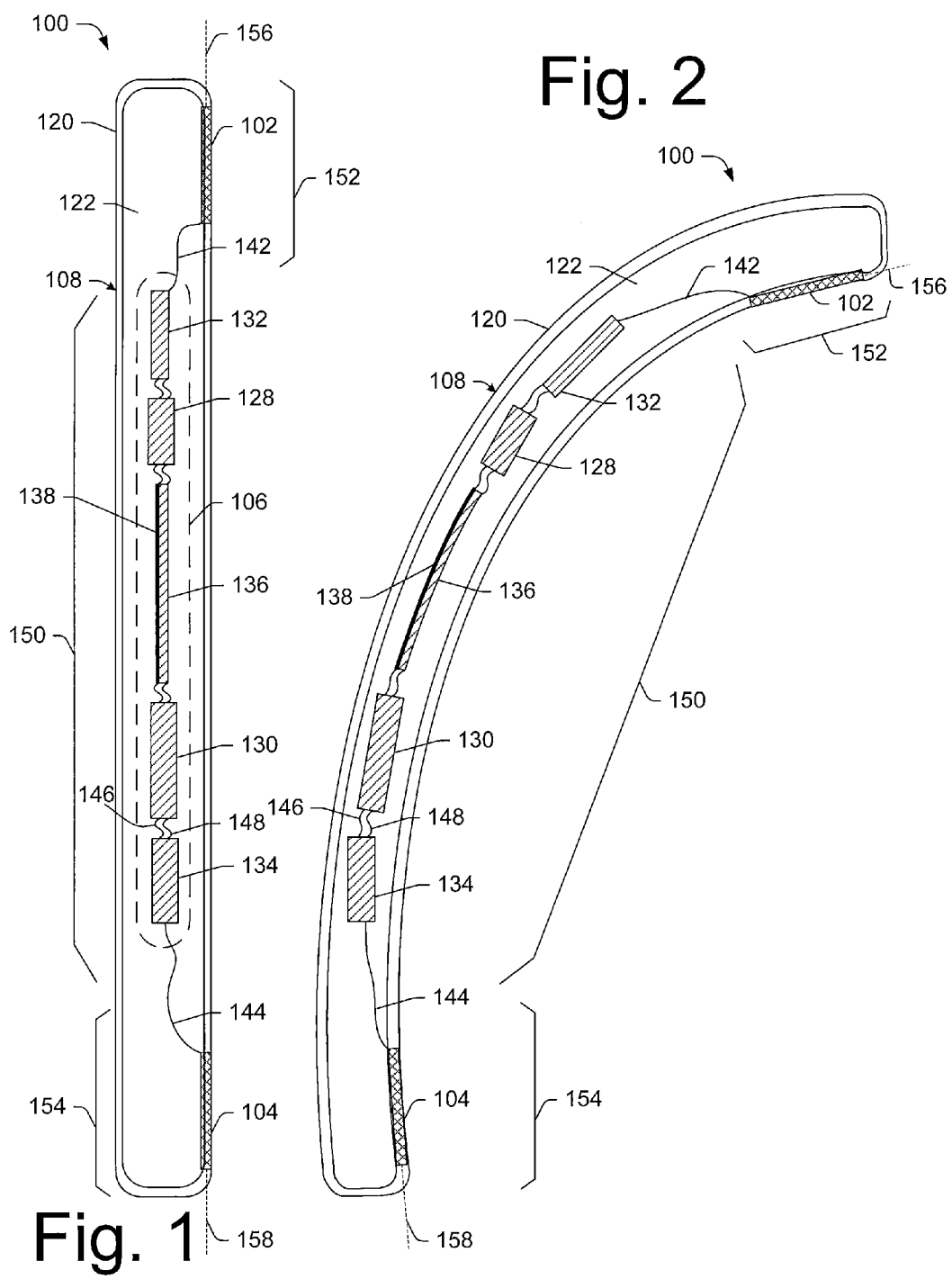

IMPLANTABLE MEDICAL DEVICE

CROSS-REFERENCE TO RELATED APPLICATIONS

This application is related to U.S. patent application Ser. No. 11/553,816, filed concurrently herewith, titled "CONFIGURABLE IMPLANTABLE MEDICAL DEVICE" now abandoned; and U.S. patent application Ser. No. 11/553,859, filed concurrently herewith, titled "PERICARDIAL CARDIOVERTER DEFIBRILLATOR" still pending.

TECHNICAL FIELD

The present invention generally relates to implantable medical devices.

BACKGROUND

Implantable medical devices are utilized in various patient scenarios. For instance, in cardiac scenarios, implantable medical devices (IMDs) are utilized to gather patient data regarding cardiac function and/or to stimulate the patient's heart. In an obesity scenario the IMD can gather data from around the stomach and provide stimulation to the same region. In a neurogenic bladder scenario the IMD can gather data from around the bladder and provide stimulation to the same region including the pudendal and pelvic nerves. In many of these scenarios, the IMD consists of a base unit or "can" positioned distal to the patient's target tissue and one or more electrodes positioned proximate the patient's target tissue and connected to the base unit via an insulated lead(s). While such IMDs have gained acceptance, efforts continue at alternative IMD designs.

SUMMARY

Techniques related to implantable medical devices (IMDs) are described. One such IMD includes first and second electrodes and a continuous body joined with and extending between the electrodes. Processing electronics are located within the body and are coupled with the first and second electrodes.

BRIEF DESCRIPTION OF THE DRAWINGS

The Figures are provided for discussion purposes and may not be drawn to scale.

FIGS. 1-2 illustrate sectional views of an exemplary implantable medical device in accordance with one implementation.

DETAILED DESCRIPTION

Overview

Figure 3:
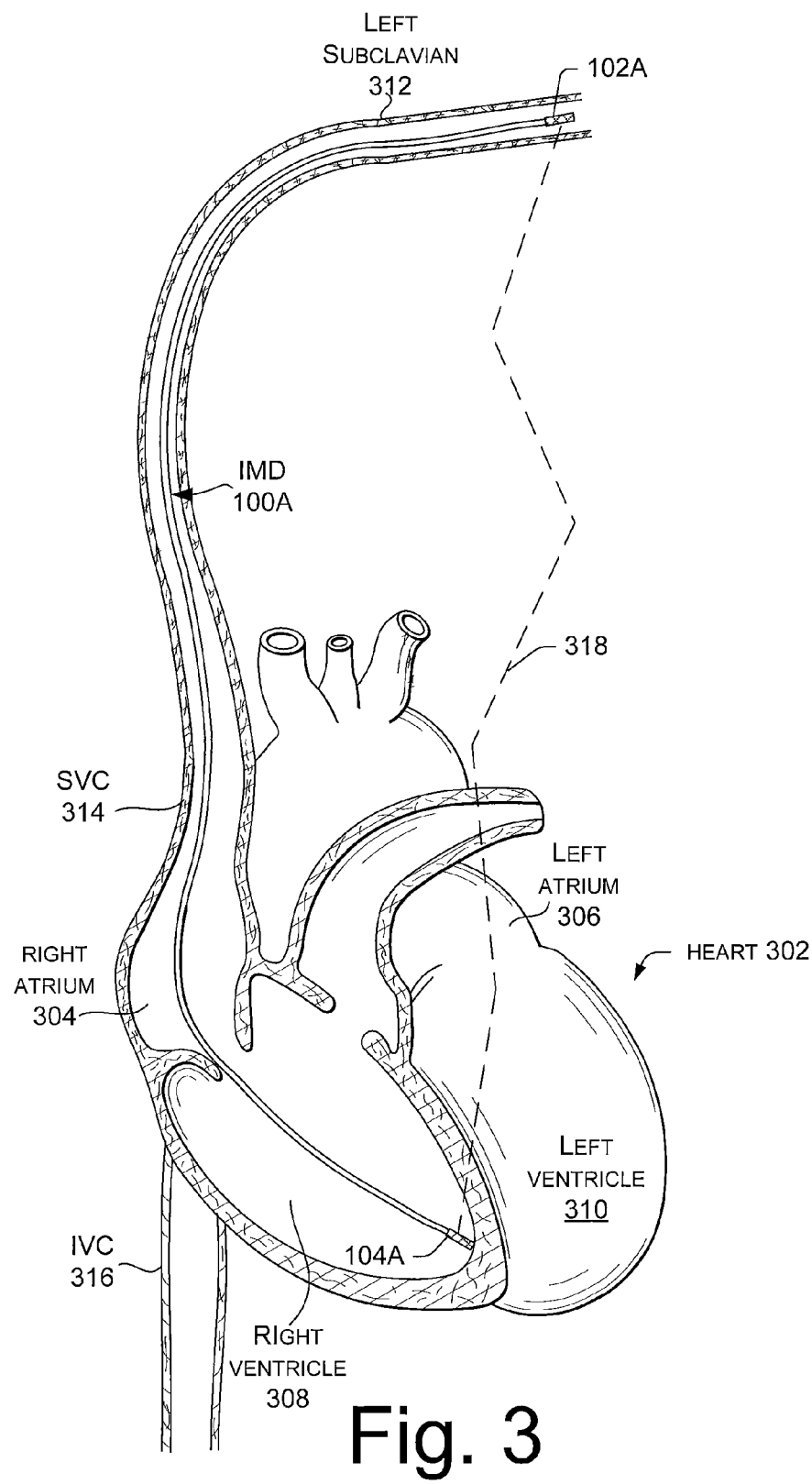
FIGS. 3-6 illustrates perspective views of exemplary implantable medical devices in accordance with one implementation.

The following discussion describes techniques related to implantable medical devices (IMDs). Implantable medical devices can be utilized to monitor and/or deliver therapy to a target tissue. Examples of target tissues can include various organs, portions of organs, and/or organ systems. For instance, an IMD may be directed to a particular nerve and/or to the central nervous system, or to the heart and/or portions of the nervous system, such as the phrenic nerve. Examples of other target tissues include, but are not limited to, organs of the digestive system, such as the pancreas, and bladder, among others. Several examples of exemplary IMDs and associated techniques are described below in a cardiac related context.

Some exemplary IMDs are configured to be inserted into the patient's vasculature and to be positioned in the vasculature in an orientation that allows sensing of the target tissue. In some cases an entirety of the IMD is configured to be positioned in the patient's vasculature proximate the target tissue. In other cases, a portion of the IMD is positioned in the vasculature and a different portion is positioned outside the vasculature such as in the target tissue.

In but one example, an exemplary IMD includes a pair of sensing mechanisms or electrodes for sensing patient data. A flexible body extends between the electrodes and houses various electronic components, such as components for storing sensed patient data. Some exemplary IMDs are flexible yet are predisposed to a desired configuration which can contribute to physically maintaining the IMD proximate the target tissue while allowing natural patient movement. Further examples of exemplary IMDs are described in more detail below.

Implantable Medical Devices

FIGS. 1-2 illustrate an exemplary implantable medical device (IMD) 100. In this illustrated configuration, IMD 100 includes sensing mechanisms in the form of two conductive electrodes 102 and 104 which are electrically coupled to electronic components indicated generally at 106. IMD 100 also includes a flexible body 108 which continuously extends between the conductive electrodes and within which the electronic components 106 reside.

IMD 100 includes a surface material 120 and a base material 122. The electronic components 106 include a power source, memory, and/or processing capabilities. In this instance, the power source is in the form of batteries 128, 130. Other electronic components include capacitors 132, 134, and an integrated circuit 136 which is formed on a substrate 138. In this case, integrated circuit 136 provides both processing and memory capabilities to IMD 100. Conductors 142, 144 interconnect electrodes 102, 104 respectively with electronic components 106. Conductors 146, 148 interconnect various electronic components 106 (not all of the conductors 146, 148 are designated with specificity).

In the illustrated IMD configuration, the electrodes 102, 104 generally define opposing ends of the IMD with the flexible body 108 extending therebetween. Surface material 120 is positioned over the IMD and serves to protect the electronic components 106. For instance, in some cases, surface material 120 physically protects the electronic components 106 as well as providing corrosion protection and electrical insulation to the IMD to avoid short circuits involving the electronic components 106 and/or electrical connections between individual electronic components and the electrodes 102, 104.

In various configurations, the surface material 120 can be either electrically insulative, electrically conductive or a combination thereof. In the illustrated example, the surface material is an electrically insulative material which can have various anti-clotting and/or anti-epithelial compounds positioned thereon. The electrodes 102, 104 are exposed through the surface material 120 to facilitate electrical connectivity with patient tissues. In another case, an electrically insulative surface material can extend over the electrodes but can be doped over the electrodes to facilitate electrical connectivity between patient tissues and the electrodes. Other sensing mechanisms can be utilized which need not be in electrical communication with the patient's tissues. For instance, a pressure sensing mechanism can sense a patient condition (e.g., blood pressure) through an electrically insulative surface material.

In the illustrated configuration, electronic components 106 are positioned in base material 122 over which surface material 120 is formed. Other implementations can utilize a homogeneous construction where a single material acts as both the base material and the surface material. For instance, the electronic components 106, electrodes 102, 104 and associated conductors 142, 144, 146 and 148 can be positioned into an injection mold and a flexible polymer can be injected into the mold to hermetically seal the IMD while allowing the electrodes to be exposed for purposes of receiving and/or sending electrical signals. In another scenario, the base material 122 may be preformed to accept the electronics and electrodes. The surface material 120 can be positioned over the base material after the electronics 106 and electrodes 102, 104 are positioned therein.

As mentioned above, IMD 100 includes a flexible body 108 which continuously extends between the conductive electrodes and within which electronic components 106 reside. The electronic components give the IMD sensing, processing and memory capabilities sufficient to allow the IMD to function as a self-contained unit which can sense and store patient data. In such instances, the IMD may be thought of as a self-contained 'can-less lead' or 'device-less lead' which has the capability to perform the functionality of sensing and/or providing therapy associated with a traditional IMD. These exemplary can-less leads achieve an IMD functionality without a separate can or housing which contains the electronic components and to which traditional lead(s) are attached during implantation. As should be recognized by the skilled artisan the can-less lead reduces or eliminates any need to interconnect IMD components during implantation. For instance, the can-less lead eliminates the lead-to-can interconnection which traditionally is made during implantation. Instead, the can-less lead can be implemented as a factory formed unit which can be easier to implant and have lowered failure rates than traditional IMD configurations. For example, there is a higher likelihood of hermetically sealing an exemplary IMD in the controlled conditions of a factory setting as opposed to an operating room during implantation.

IMD 100 has a flexible nature which facilitates implantation of the IMD. Further, once implanted, the flexible nature allows the IMD to flex with patient movement and to avoid patient discomfort and/or dislodgement. Alternatively or additionally, the flexible nature allows the IMD to more easily configure to available spaces in the patient. For instance, the flexible nature can allow the IMD to configure to the patient's vasculature and/or other tissue rather than displacing patient tissues as can occur with more rigid configurations.

IMD 100 is flexible at least along a region 150 of body 108 as evidenced by comparing FIG. 1 and FIG. 2. In the illustrated configuration, the flexibility allows end regions 152, 154 to be oriented generally parallel in the configuration of FIG. 1 and obliquely in the configuration of FIG. 2. The relative orientations of the end regions can be described in relation to axes 156, 158. Axis 156 extends through electrode 102 and axis 158 extends through electrode 104. In the scenario of FIG. 1, the two axes 156, 158 are generally parallel (and generally co-extensive). In FIG. 2, axis 156 is obliquely oriented relative to axis 158.

Flexibility of the IMD can be accomplished through flexibility of the body 108 and/or electronic components 106. In some configurations, individual electronic components 106 can be flexible to aid flexure of the IMD. In this particular illustrated configuration, integrated circuit 136 is flexible, while batteries 128, 130 and capacitors 132, 134 are generally inflexible. Individual electronic components which are generally inflexible can be of a suitably short length along a length of the IMD 100 so as not to significantly impair the overall flexibility of the IMD. Further, the electronic components 106 can be separated by a distance sufficient to allow flexing of the IMD between the individual electronic components.

The integrated circuit 136 is positioned over flexible substrate 138. Some techniques for manufacturing flexible substrates form components or circuitry upon the flexible substrate 138 whereas other techniques position formed electronic components onto the flexible substrate. Various technologies for forming electronic components, such as semiconductor circuitry, upon a flexible substrate should be recognized by the skilled artisan. For instance, some technologies employ conventional substrates which are thin enough to be flexible. Various circuitry is formed over the conventional flexible substrate which is then coupled to a second flexible substrate, such as a polymer. Other technologies utilize a polymer substrate over which various materials are deposited and patterned to form the desired circuitry. Still other implementations may manufacture desired electronic components in a traditional manner as discrete units and then couple the discrete units utilizing a flexible material such as a polyimide as a common flexible substrate. In this particular instance, at least some of the electronic components are formed upon the flexible substrate during a manufacturing process to form the integrated circuit. Other techniques for forming flexible integrated circuits employ flexible polymer transistors, among others.

For purposes of explanation, consider the following scenario which illustrates an example of the flexible nature of IMD 100 as evidenced during an implantation procedure. A clinician may manipulate the IMD into a generally linear configuration as is illustrated in FIG. 1 to facilitate passing the IMD through a relatively small incision and into the patient's vasculature. Further, the flexible nature of the IMD can facilitate snaking the IMD through the vasculature until the IMD is proximate the target tissue. The clinician can then position one of the electrodes 102 or 104 proximate the target tissue. The clinician can manipulate the IMD to position the other of the electrodes 102, 104 proximate the target tissue. The flexible nature allows the IMD to follow the target tissue's shape, and/or to conform to an available space such as is offered by the vasculature, rather than imposing an external shape upon the target tissue or vasculature. Further, once implanted, the flexible nature of IMD 100 can allow the target tissue to function in a relatively normal manner including contracting, expanding, and/or distending.

As mentioned above, IMD 100 is generally flexible along its length. In this case, IMD's body 108 is flexible in a manner which is flexibly or reboundably biased along its length. The IMD is reboundably biased in that it is predisposed to assume a first configuration yet can be flexed to other configurations and then is predisposed to return to the first configuration.

For discussion purposes assume that FIG. 2 represents the predisposed configuration for IMD 100. In this instance, region 150 of body 108 can be characterized as being flexibly biased. Region 150 is interposed between the two end regions 152, 154. The flexible bias allows IMD 100 to be manipulated into the configuration of FIG. 1 and to subsequently return to the predisposed configuration of FIG. 2.

Various techniques can be utilized to contribute to the IMD 100 having a flexibly biased nature to a predisposed configuration. For instance, the IMD can include materials which tend to assume certain shapes under specific conditions. For instance, an exemplary flexible IMD can include a shape memory alloy in a manner which contributes to the IMD assuming a desired predisposed configuration when implanted in the patient. For example, strips of a shape memory alloy could be added to the IMD, such as during the molding process described above, so that the shape memory alloy has a tendency to assume a desired shape due to conditions experienced when implanted in the patient's body. Such conditions could be related to the patient's internal temperature and/or could be facilitated by the clinician once the IMD is positioned proximate the target tissue by the clinician. The shape memory alloy then contributes to the overall IMD having a tendency to assume the desired configuration.

Still another exemplary technique for forming an IMD which is flexibly biased to assume a desired configuration entails molding the IMD in the desired configuration. For instance, the electrodes and electronic components can be positioned in a mold of a desired shape or configuration for the IMD. A polymer or other suitable material can be injected into the mold and cured to form the IMD in the desired shape. The IMD would be predisposed to assume the desired shape yet would have a flexible nature which could be manipulated into other configurations. The skilled artisan should recognize other techniques consistent with these examples.

Consider further another implantation scenario where IMD 100 is flexibly predisposed to assume a desired configuration. For instance, assume that it is determined that a desired configuration for IMD 100 is the configuration illustrated in FIG. 2. During implantation, the clinician can manipulate the IMD into a configuration other than the desired configuration, such as the configuration illustrated in FIG. 1. In some implementations, the IMD's predisposition to assume the desired configuration is strong enough that once the clinician stops manipulating it, the IMD assumes the desired configuration of FIG. 2. Stated another way, once the clinician stops exerting force upon the IMD, the IMD rebounds to its predisposed configuration. In other implementations, the clinician manipulates and/or assists the IMD back into the desired configuration.

The IMD's flexibly biased nature can allow the configurable IMD to flex, such as when exposed to external forces (e.g. forces caused by patient movement and/or bodily processes), and then the predisposition can be sufficient to return the IMD to the desired configuration upon removal or reduction of the force. Such flexibly biased implementations may further aid in maintaining the IMD proximate the target tissue, such as will be discussed below in relation to FIGS. 3-6.

FIGS. 3-6 illustrate additional exemplary IMDs in a cardiac setting. In these implementations, IMDs 100A, 100B, 100C, and 100D respectively are positioned to sense data from a patient's heart 302. In relation to heart 302, the right atrium is designated as 304, the left atrium is designated as 306, the right ventricle is designated as 308, and the left ventricle is designated as 310. Further designated are the left subclavian vein 312, superior vena cava (SVC) 314, and the inferior vena cava (IVC) 316.

FIG. 3 illustrates IMD 100A which includes two electrodes 102A, 104A positioned at opposing ends of the IMD. In this instance, the IMD extends from the patient's vasculature and into the target cardiac tissue. Specifically in this case, the IMD extends from the left subclavian vein 312, through the superior vena cava 314, into the right atrium 304, and the right ventricle 308. Electrode 102A is positioned in the subclavian vein 312 while electrode 104A is positioned in the heart's right ventricle 308. The relative positions of the electrodes 102A, 104A allow electrical conduction between the two electrodes through the target tissue. For instance, for discussion purposes one such hypothetical path of electrical conduction is represented generally at 318.

IMD 100A is flexible in nature along its length extending between electrodes 102A, 104A. The flexible nature allows the IMD to conform to a shape of the patient's vasculature and/or target tissue and to flex with patient movements which may dislodge more rigid IMDs. Further, IMD 100A is a single hermetically sealed unit which does not have any connections where a clinician interconnects various components during implantation. Interconnections often prove problematic as failure points of an IMD due to mechanical breakage and/or electrical short circuits. Furthermore, interconnections are often subject to clotting and/or epithelial build-up. Contrastingly, IMD 100A is a single self-contained factory sealed unit.

FIG. 3 illustrates a first example where an entirety of the IMD 100A can be positioned proximate a target tissue (e.g., in the heart and proximate vasculature). Positioning the entire IMD proximate the target tissue eliminates leads extending between electrodes positioned in or proximate the heart and a base or control unit positioned distally from the heart, such as in a pectoral pocket.

Positioning the entire IMD proximate the target tissue (e.g., the heart) may be a simpler procedure than traditional configurations. For instance, in traditional implantations the leads are tunneled through patient tissue so that they extend between the control unit and the electrodes. The present implementations reduce or avoid tunneling, and as such, may speed patient recovery and/or lessen patient discomfort. Further, traditional leads which are tunneled through patient tissue are subject to mechanical breakage and/or corrosion along the leads and/or where the lead interconnects with the control unit. Implantation of the present IMDs may be further simplified in that the flexible nature conforms to subtle variations in heart shape of an individual patient in contrast to rigid IMDs or rigid base units. Further, IMD 100A can be inserted into the vasculature in any suitable location utilizing known techniques.

IMD 100A, like IMD 100 described above in relation to FIGS. 1-2, has a generally uniform width along its length. The generally uniform width can reduce a likelihood of the IMD contributing to occlusion of the vessels in which the IMD is positioned. Traditional IMD configurations employ narrow leads connected to a wider control unit. The control unit may act as a bottleneck or constriction point which can cause occlusion of the vessel within which the control unit is positioned. Attempts to expand the vessel to accommodate the control unit can weaken the vessel increasing a likelihood of vessel rupture.

Figure 4:
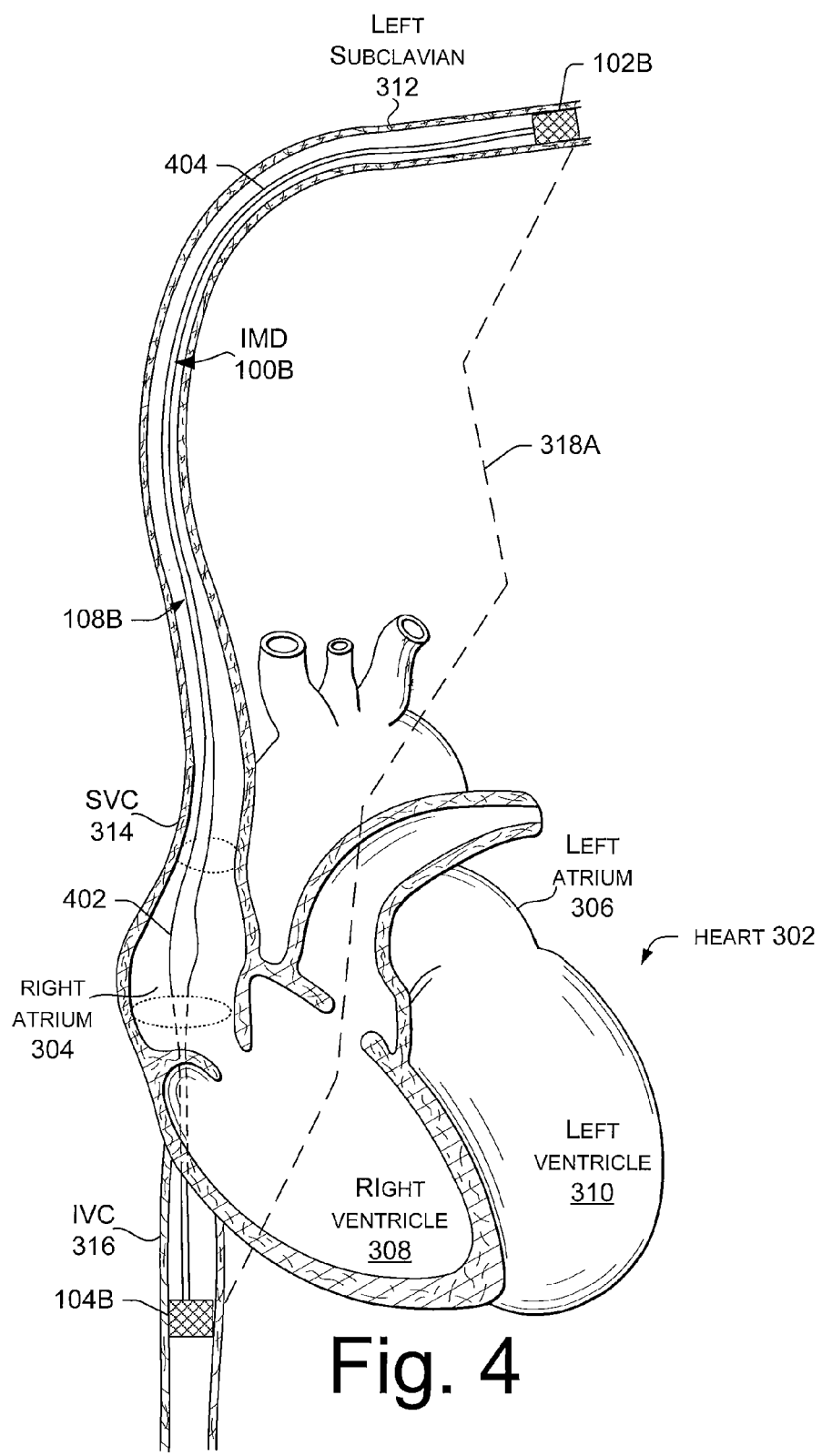

FIG. 4 illustrates another IMD 100B. In this instance, IMD 100B can sense cardiac data while the IMD is positioned in the vasculature. In this case, the IMD has a first electrode 102B positioned in the left subclavian vein 312. The IMD extends down through the superior vena cava 314 and into the inferior vena cava 316. A second electrode 104B is positioned in the inferior vena cava 316. The location of the electrodes 102B, 104B provides for electrical connectivity through heart 302 as represented generally at 318A.

In this illustrated configuration, the electrodes 102B, 104B are open ended tubes and are intended to line an interior surface of the respective vessels such that blood flows through the electrodes rather than around them. During implantation, a clinician can position an individual electrode in a desired location and then expand the electrode against the vessel wall to anchor the electrode and ultimately the IMD in the desired location. Suitable construction material for the electrodes and implantation techniques should be recognized by the skilled artisan. In this configuration, electrodes 102B, 104B are wider than a remainder of the IMD as defined by insulative portion 108B. Further, the insulative portion has wider regions 402 and narrower regions 404. Electronic components (specifically designated in FIGS. 1-2) may be more concentrated in the wider regions 402 that in narrower regions 404. Further, in this particular configuration, wider regions 402 and narrower regions 404 are strategically selected to emulate the relative dimensions of the vasculature in which the IMD is positioned. For instance, wider region 402 is positioned in the right atrium 304 while narrower region 404 is positioned in the left subclavian vein 312. The right atrium 304 is much wider relative to the left subclavian vein 312 and as such the IMD can be wider in the right atrium with reduced risk of causing occlusion. Other implementations may have wider regions of the IMD in the vasculature proximate the heart, such as the superior or inferior vena cava, and narrower regions in distal vasculature, such as the subclavian or femoral vein, to reduce constriction of the blood flow and resultant consequences. While these examples illustrate placement of the IMD in the veins, other implementations can position the IMDs in the arteries.

Figure 5:
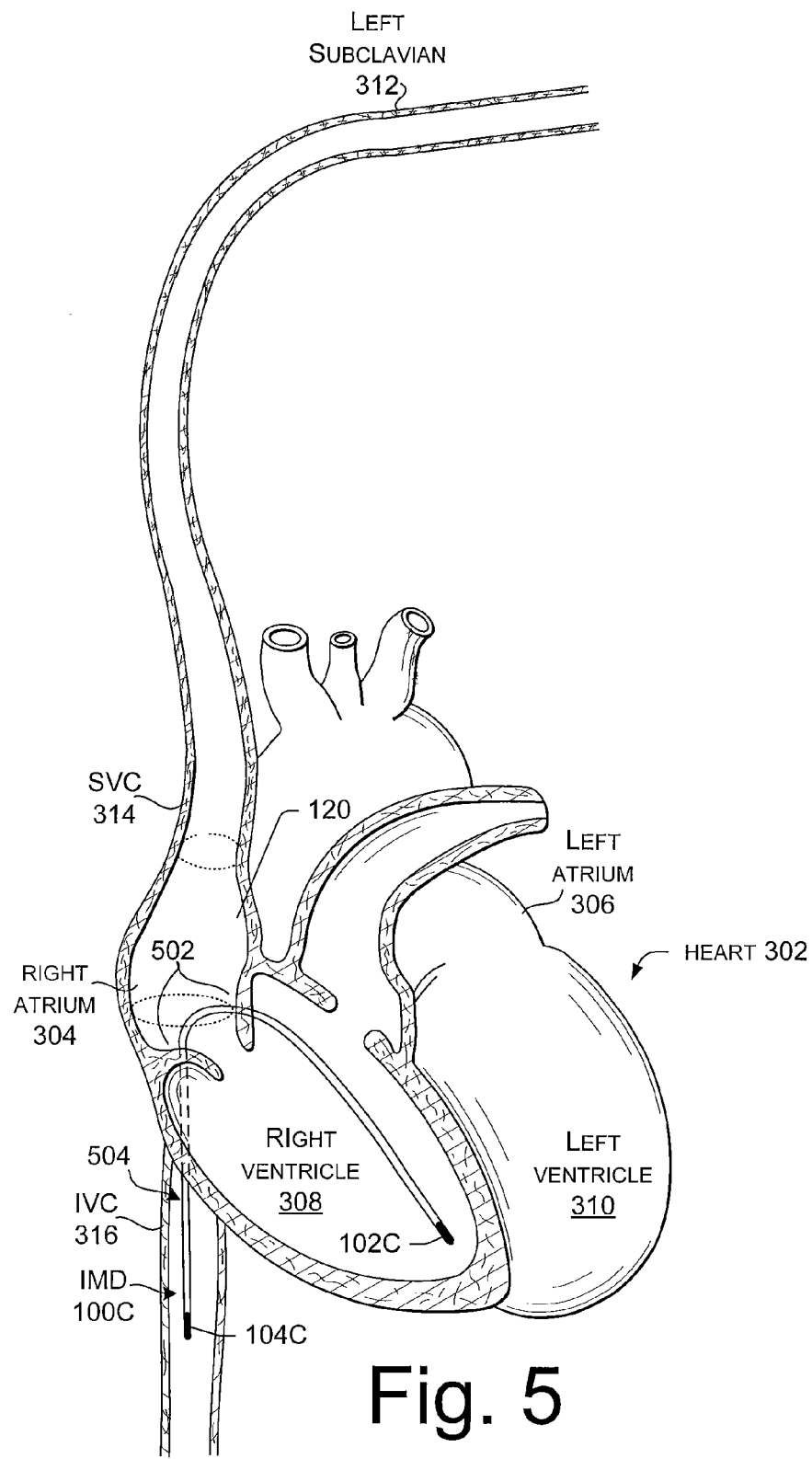

FIG. 5 illustrates IMD 100C which, in this instance, is positioned extending from the inferior vena cava through the right atrium 304 and into the right ventricle 308. IMD 100C offers an example of an IMD being predisposed to a desired configuration. In this instance, the desired configuration involves at least a region 502 of the IMD's body 504 located in the right atrium 304 being bent effective to position electrode 102C in the right ventricle 308 and electrode 104C in the inferior vena cava 316. Further, IMD 100C is reboundably biased to maintain the illustrated predisposed configuration. In this case, the bias is manifested at least in region 502. The bias can aid in maintaining the IMD in the illustrated orientation relative to the heart and vasculature. In comparison a flexible IMD lacking a predisposed configuration may be dislodged from the heart by the heart's alternating expansion and contraction and/or patient movements. The predisposition may reduce stress upon and/or entirely eliminate a need for traditional anchoring techniques (examples of which are described in relation to FIGS. 4 and 6).

IMD 100C, as illustrated in FIG. 5, may be generally circular, elliptical or other shape when viewed transverse a length of the IMD. The length can be thought of as extending between the two electrodes 102C, 104C as defined by body 504. In some implementations, the generally circular configuration may allow the IMD to more readily conform to the target tissue. For instance, the generally circular configuration may be generally flexible in relation to any axis which is transverse the long axis. Accordingly, if patient movements apply a force to the IMD in a direction transverse the length, the IMD is likely to be able to flex in the direction of the force rather than binding or coming dislodged from the target tissue. In some of these implementations the IMD may have similar flexibility along any transverse axis such that the IMD can readily conform to patient movements and avoid incidences of twisting or binding such as when the IMD is exposed to forces in several directions at once.

Figure 6:
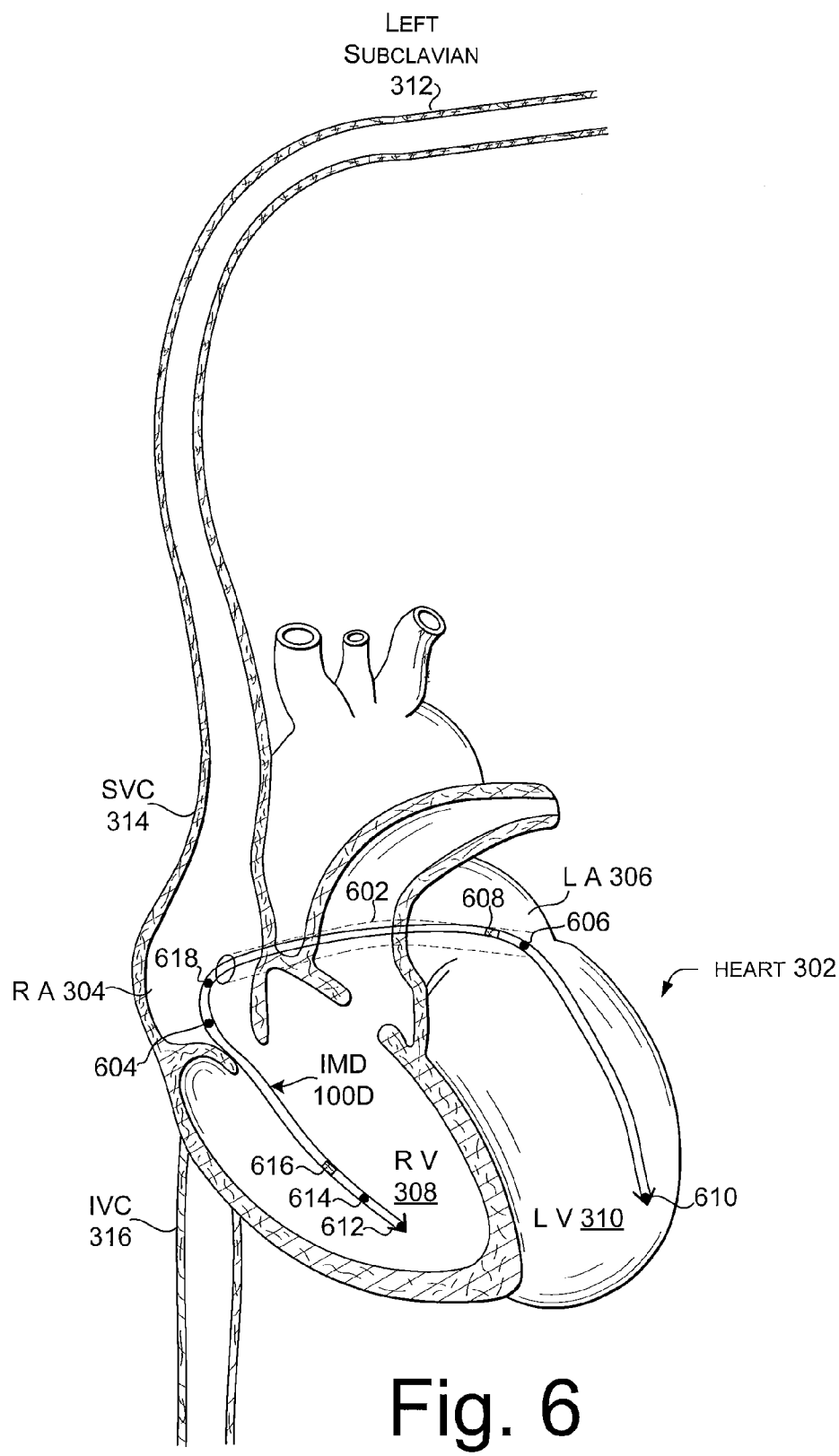

FIG. 6 illustrates still another exemplary IMD manifested as IMD 100D which is positioned within a target tissue (e.g., patient's heart 302). In this case IMD 100D is sufficiently flexible to access both the left and right chambers of the heart by passing through cardiac vein 602. IMD 100D has electrodes positioned adjacent to, or in, each chamber of the heart 304, 306, 308, and 310.

For instance, a right atrial electrode 604 is positioned adjacent the right atrium 304. The right atrial electrode 604 enables the device to sense atrial cardiac signals and apply pacing therapy proximate to the right atrium 304.

A left atrial pacing electrode 606 is employed for applying left atrial pacing therapy to the left atrium 306, while a left atrial shocking electrode 608 is positioned adjacent the left atrium to apply shocking therapy. A left ventricular electrode 610 is positioned adjacent to the left ventricle 310 to sense ventricular cardiac signals and deliver left ventricular pacing therapy. A right ventricular pacing electrode 612, a right ventricular sensing electrode 614, and a right ventricular shocking electrode 616 are positioned adjacent the right ventricle 308. Further, a superior vena cava (SVC) electrode 618 is positioned in the right atrium adjacent the SVC for sensing and/or shocking therapy.

Figure 7:
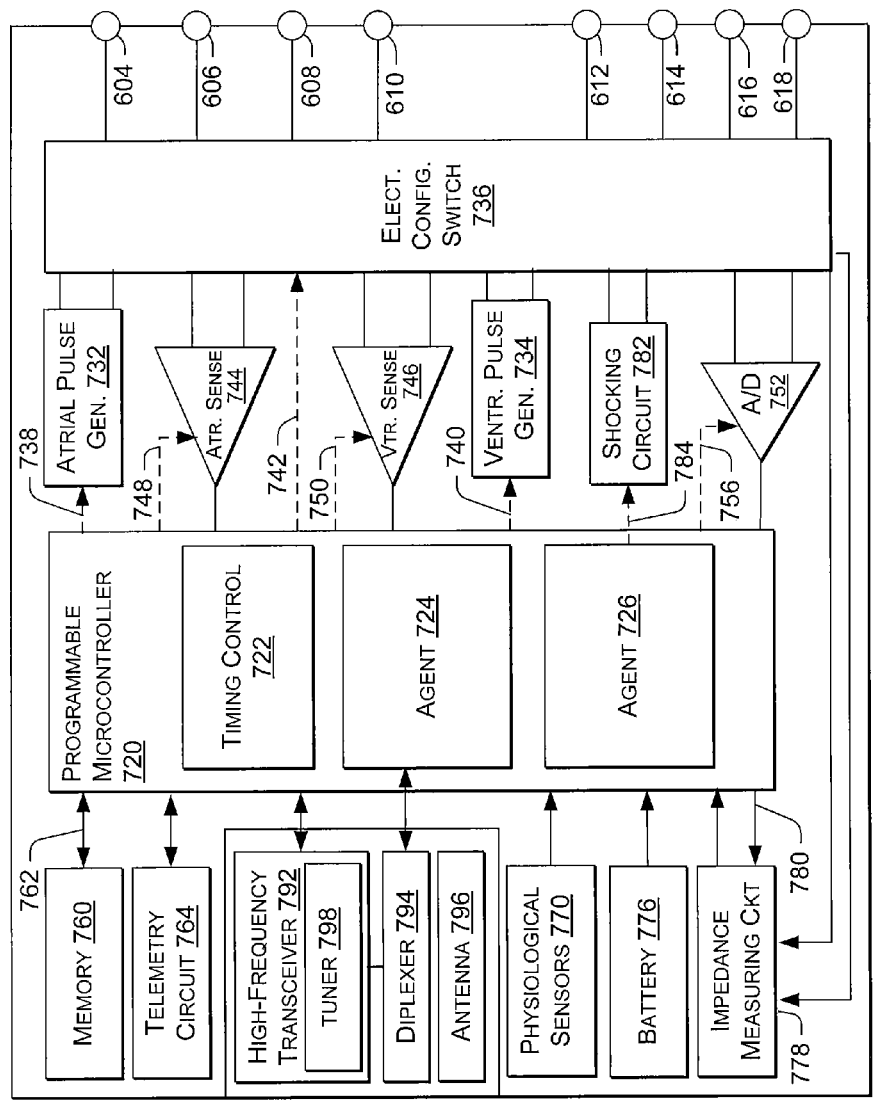
FIG. 7 illustrates a functional block diagram of an exemplary implantable medical device in accordance with one implementation.

FIG. 7 shows an exemplary, simplified block diagram depicting various components of IMD 100D. The IMD 100D can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

IMD 100D includes various circuitry and electronic components to perform the above described functionality. IMD 100D includes the electrodes described above in relation to FIG. 6. Specifically, IMD 100D includes right atrial electrode 604, left atrial pacing electrode 606, left ventricular electrode 610, right ventricular pacing electrode 612, right ventricular sensing electrode 614, right ventricular shocking electrode 616 and superior vena cava (SVC) electrode 618.

At the core of the IMD 100D is a programmable microcontroller 720 that controls various operations of the IMD, including cardiac monitoring and stimulation therapy. Microcontroller 720 includes a microprocessor (or equivalent control circuitry), RAM and/or ROM memory, logic and timing circuitry, state machine circuitry, and I/O circuitry. Microcontroller 720 includes the ability to process or monitor input signals (data) as controlled by a program code stored in a designated block of memory. Any suitable microcontroller 720 may be used.

For discussion purposes, microcontroller 720 is illustrated as including timing control circuitry 722 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and so on. Microcontroller 720 may further include a plurality of agents or modules 724, 726 that, when executed, perform various functions of the IMD 100D. For instance, the agents can perform arrhythmia detection, timing control, and/or morphology detection, among other functionalities. The agents 724, 726 may be implemented in hardware as part of the microcontroller 720, or as software/firmware instructions programmed into the device and executed on the microcontroller 720 during certain modes of operation.

The IMD 100D further includes an atrial pulse generator 732 and a ventricular pulse generator 734 that generate pacing stimulation pulses for delivery to the right atrial electrode 604, the left atrial shocking electrode 608, the left ventricle electrode 610 and the right ventricle pacing electrode 612 via electronic configuration switch 736. It is understood that in order to provide stimulation therapy in each of the four chambers of the heart, the atrial and ventricular pulse generators, 732 and 734, may include dedicated, independent pulse generators, multiplexed pulse generators, or shared pulse generators. The pulse generators 732 and 734 are controlled by the microcontroller 720 via appropriate control signals 738 and 740, respectively, to trigger or inhibit the stimulation pulses.

The electronic configuration switch 736 includes a plurality of switches for connecting the desired electrodes to the appropriate I/O circuits, thereby providing complete electrode programmability. Accordingly, switch 736, in response to a control signal 742 from the microcontroller 720, determines the polarity of the stimulation pulses (e.g., unipolar, bipolar, combipolar, etc.) by selectively closing the appropriate combination of switches (not shown).

Atrial sensing circuits 744 and ventricular sensing circuits 746 may also be selectively coupled to the right atrial electrode 604, the left atrial sensing electrode 606, the left ventricle electrode 610, and the right ventricle sensing electrode 614 to detect the presence of cardiac activity in each of the four chambers of the heart. Accordingly, the atrial (ATR. SENSE) and ventricular (VTR. SENSE) sensing circuits, 744 and 746, may include dedicated sense amplifiers, multiplexed amplifiers, or shared amplifiers. Each sensing circuit 744 and 746 may further employ one or more low power, precision amplifiers with programmable gain and/or automatic gain control, bandpass filtering, and a threshold detection circuit to selectively sense the cardiac signal of interest. The automatic gain control enables the IMD 100D to deal effectively with the difficult problem of sensing the low amplitude signal characteristics of atrial or ventricular fibrillation. Switch 736 determines the "sensing polarity" of the cardiac signal by selectively closing the appropriate switches. In this way, the clinician may program the sensing polarity independent of the stimulation polarity.

The outputs of the atrial and ventricular sensing circuits 744 and 746 are connected to the microcontroller 720 which, in turn, is able to trigger or inhibit the atrial and ventricular pulse generators 732 and 734, respectively, in a demand fashion in response to the absence or presence of cardiac activity in the appropriate chambers of the heart. The sensing circuits 744 and 746 receive control signals over signal lines 748 and 750 from the microcontroller 720 for purposes of controlling the gain, threshold, polarization charge removal circuitry (not shown), and the timing of any blocking circuitry (not shown) coupled to the inputs of the sensing circuits 744 and 746.

Cardiac signals are also applied to inputs of an analog-to-digital (ND) data acquisition system 752. The data acquisition system 752 is configured to acquire intracardiac electrogram signals, convert the raw analog data into a digital signal, and store the digital signals for later processing and/or telemetric transmission to an external device such as a programmer. The data acquisition system 752 is coupled to the right atrial electrode 604, the left atrial shocking electrode 606, the left ventricle electrode 610, and the right ventricle pacing electrode 612 through the switch 736 to sample cardiac signals across any pair of desired electrodes.

The data acquisition system 752 may be coupled to the microcontroller 720, or other detection circuitry, to detect an evoked response from the heart 302 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 720 detects a depolarization signal during a window following a stimulation pulse, the presence of which indicates that capture has occurred. The microcontroller 720 enables capture detection by triggering the ventricular pulse generator 734 to generate a stimulation pulse, starting a capture detection window using the timing control circuitry 722 within the microcontroller 720, and enabling the data acquisition system 752 via control signal 756 to sample the cardiac signal that falls in the capture detection window and, based on the amplitude, determines if capture has occurred.

The microcontroller 720 is further coupled to a memory 760 by a suitable data/address bus 762, wherein the programmable operating parameters used by the microcontroller 720 are stored and modified, as required, in order to customize the operation of the IMD 100D to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 302 within each respective tier of therapy. The operating parameters may be updated through communication with an external device, such as an IMD manager or programmer. With memory 760, the IMD 100D is able to sense and store a relatively large amount of data (e.g., from the data acquisition system 752) at specific addresses in memory 760. IMD 100D may subsequently transmit some or all of the data to external computing device(s), such as a programmer, for subsequent analysis.

Operating parameters of the IMD 100D may be non-invasively programmed into the memory 760 through a telemetry circuit 764 in telemetric communication with an external device, such as a programmer. The telemetry circuit 764 advantageously allows patient data such as intracardiac electrogram data and status information relating to the operation of the IMD 100D (as contained in the microcontroller 720 or memory 760) to be sent to the external devices.

The IMD 100D can further include one or more physiologic sensors 770, commonly referred to as "rate-responsive" sensors because they are typically used to adjust pacing stimulation rate according to the exercise state of the patient. However, the physiological sensor 770 may further be used to detect changes in cardiac output, changes in the physiological condition of the heart, or diurnal changes in activity (e.g., detecting sleep and wake states, detecting position or postural changes, etc.). Accordingly, the microcontroller 720 responds by adjusting the various pacing parameters (such as rate, AV Delay, V-V Delay, etc.) at which the atrial and ventricular pulse generators, 732 and 734, generate stimulation pulses. Examples of physiologic sensors that may be implemented in IMD 100D include known sensors that, for example, sense respiration rate and/or minute ventilation, pH of blood, ventricular gradient, and so forth.

The IMD 100D additionally includes a. power source in the form of a battery 776 that provides operating power to all of circuits shown in FIG. 7. If the IMD 100D is configured to deliver pacing or shocking therapy, the battery 776 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 776 also desirably has a predictable discharge characteristic so that elective replacement time can be detected.

As one example, the IMD 100D employs lithium/silver vanadium oxide batteries. Other types of power sources can alternatively be utilized.

While a single power source is mentioned here, this is but one configuration. For example, the IMD could have power sources in individual regions. For instance, electrodes proximate each chamber of the heart may have their own power supply. In another example, the sensing electrodes have a dedicated power supply, the pacing electrodes have another dedicated power supply, while the shocking electrodes have still another different dedicated power supply.

The IMD 100D can further include magnet detection circuitry (not shown), coupled to the microcontroller 720, to detect when a magnet is placed over the IMD. A magnet may be used by a clinician to perform various test functions of the IMD 100D and/or to signal the microcontroller 720 that an external programmer is in place to receive or transmit data to the microcontroller 720 through the telemetry circuits 764.

The IMD 100D further includes an impedance measuring circuit 778 that is enabled by the microcontroller 720 via a control signal 780. Uses for an impedance measuring circuit 778 include, but are not limited to, electrode impedance surveillance during the acute and chronic phases for proper electrode positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 778 is advantageously coupled to the switch 736 so that any desired electrode may be used.

In the case where the IMD 100D is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 720 further controls a voltage delivery circuit or shock circuit 782 by way of a control signal 784. The shocking circuit 782 generates shocking pulses of low (up to 0.5 joules), moderate (0.5-10 joules), or high energy (11 to 40 joules), as controlled by the microcontroller 720. Such shocking pulses are applied to the patient's heart through at least two shocking electrodes, and as shown in this implementation, selected from the left atrial shocking electrode 608, the right ventricle shocking electrode 616, and/or the SVC electrode 618.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 720 is capable of controlling the synchronous or asynchronous delivery of the shocking pulses.

The IMD 100D is further designed with the ability to support high-frequency wireless communication, typically in the radio frequency (RF) range. The IMD 100D is equipped with a high-frequency transceiver 792 and a diplexer 794. High-frequency signals received by a dedicated antenna 796, or one or more of the electrodes, are passed to the transceiver 792 directly, or via diplexer 794. The high-frequency transceiver 792 may be configured to operate on one or a few frequencies. Alternatively, the transceiver 792 may include a tuner 798 that tunes to various frequencies when attempting to establish communication links with the external communication device (e.g., IMD manager, programmer, local transceiver, etc.). The wireless communication capabilities allow IMD 100D to function as an apparatus within a patient care system that can also include various external devices such the programmer or device manager.

Exemplary Processes/Techniques

Figure 8:
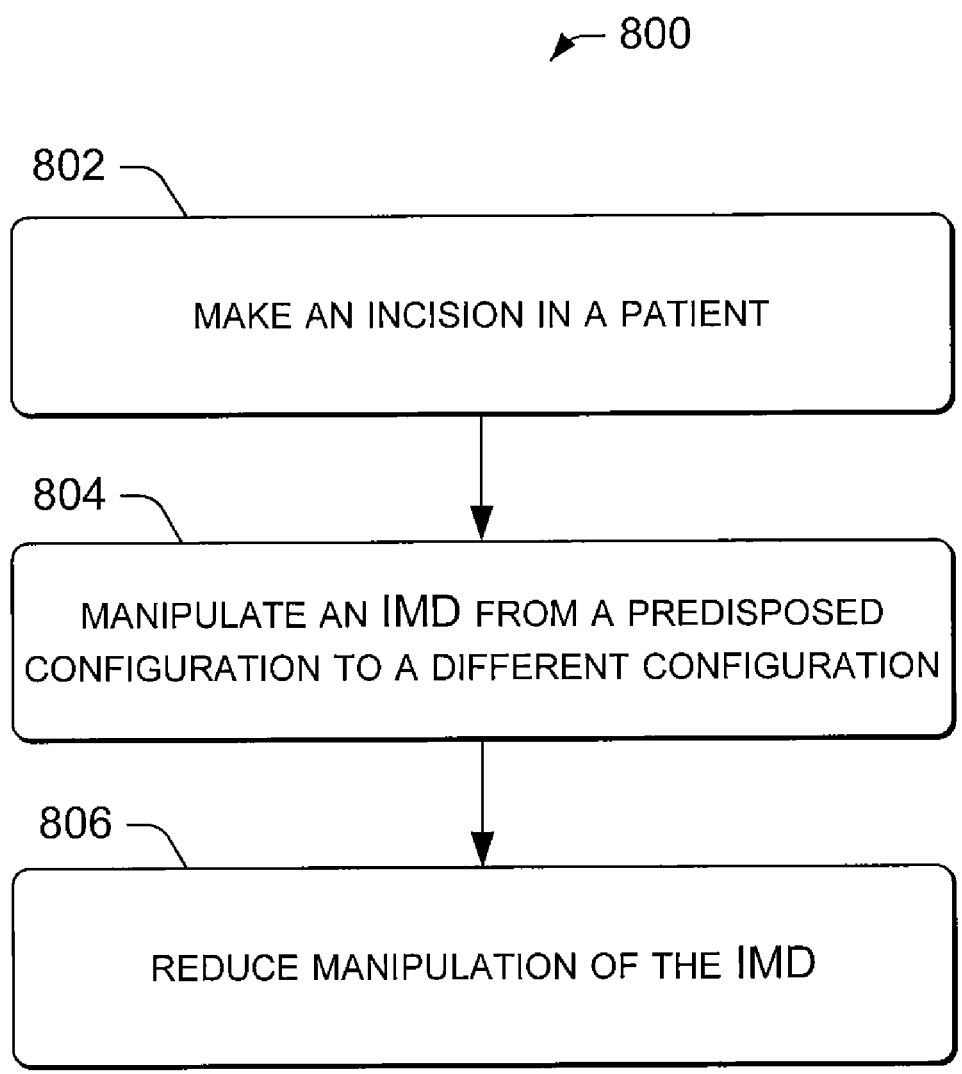
FIG. 8 is a flow diagram of an exemplary implantation technique for an implantable medical device in accordance with one implementation.

FIG. 8 illustrates one exemplary process 800 for implanting an IMD. The order in which the process is described is not intended to be construed as a limitation, and any number of the described process blocks can be combined in any order to implement the process.

At block 802, an incision is made in a patient. The incision may correlate to a standard operation technique such as a thoracoscopic procedure. For instance, some techniques make an incision that exposes a vessel to allow insertion of the IMD into the vessel.

At block 804, an IMD is manipulated from a predisposed configuration to a different configuration during implantation of the IMD into the patient. For instance, the IMD's predisposed configuration can entail a portion or entirety of the IMD being curvilinear. The IMD may be manipulated into a generally linear configuration which aids in getting the IMD proximate the target tissue. In one technique, the IMD may be manipulated into or through the use of a thoracoscopic instrument utilized in the implantation procedure. In some scenarios, the IMD is manipulated in order to position the IMD's electrodes in desired locations relative to the target tissue. Examples, of such electrode locations are described above in relation to FIGS. 3-6.

In some cases the IMD is a hermetically-sealed self-contained lead that does not require the clinician to physically interconnect component parts during the implantation procedure. Such a self-contained IMD can have reduced incidence of failure when compared to traditional IMDs. For example, connections and/or sealing procedures performed in a factory setting can be made under more controlled conditions than can be maintained in an operating room scenario.

At block 806, the manipulation of the IMD is reduced to allow the IMD to return to the predisposed configuration. In one scenario, once the electrodes are positioned as desired, manipulation of the IMD ceases and the IMD returns to its predisposed configuration. In other instances, various actions may be undertaken to aid the IMD in achieving the predisposed configuration. For instance, the clinician may apply a force to aid the IMD in returning to the predisposed configuration. Alternatively or additionally, in relation to IMDs which incorporate shape memory alloys, some action may be taken to cause the shape memory alloy to return to the predisposed configuration. In other instances, in vivo conditions, such as the body temperature or pH, may act upon the shape memory alloys to effectuate configuration change. Once the IMD assumes the predisposed configuration, its flexibility allows for greater freedom of patient movement and decreases any risk of the electrodes being displaced by patient activity, among other advantages. In one such scenario, patient movement, such as when a patient bends, can cause the IMD to flex with the patient's tissue from the predisposed configuration into another different condition. When the patient straightens, the IMD assumes the predisposed configuration. Having a bias to a predisposed configuration can also aid in maintaining the IMD in a desired location and orientation in the patient to allow the IMD to sense and/or provide therapy to the patient. One such example is described above in relation to FIG. 5.

CONCLUSION

The foregoing discussion describes techniques related to IMDs. Although the inventive principles have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. An implantable medical device configured for entire placement within a heart, said device comprising:
   a single flexible body having a first terminal end spaced apart from and opposite a second terminal end;
   at least four conductive electrodes linearly spaced apart from each other along the length of the single flexible body and configured to be positioned in electrical communication with a target tissue of a patient; and
   electronic components comprising a battery, a capacitor and an integrated circuit, contained within the single flexible body, at least one of the components being selectively electrically coupled to the at least four conductive electrodes to receive electrical signals therefrom;
   wherein the single flexible body has a length that allows for entire residence within the heart, including residence of the first terminal end in a patient's blood vessel over the left side of the heart, and residence of the second terminal end within the right ventricle, and the at least four electrodes are spaced apart so as to place a first electrode over the left ventricle, a second electrode over the left atrium, a third electrode within the right atrium and a fourth electrode within the right ventricle.

2. The implantable medical device as recited in claim 1, wherein the electronic components are further configured to deliver electrical signals to the at least four conductive electrodes.

3. The implantable medical device as recited in claim 1, wherein the single flexible body is generally tubular shaped along the length.

4. The implantable medical device as recited in claim 1, wherein the single flexible body has generally uniform transverse dimensions along the length.

5. The implantable medical device as recited in claim 1, wherein the electronic components are arranged linearly within the single flexible body.

6. The implantable medical device as recited in claim 1, wherein individual electronic components are flexible along the length of the single flexible body.

7. The implantable medical device as recited in claim 1, wherein at least some of the electronic components are positioned over a flexible substrate.

8. The implantable medical device as recited in claim 7, wherein at least some of the electronic components positioned over the flexible substrate are formed upon the flexible substrate.

9. The implantable medical device as recited in claim 1, wherein at least one individual electrode is configured to physically contact the target tissue.

10. The implantable medical device as recited in claim 1, wherein at least a portion of the single flexible body is predisposed to assume a desired configuration.

* * * * *